US012729171B2

(12) United States Patent
Fu et al.

(10) Patent No.: US 12,729,171 B2
(45) Date of Patent: Sep. 8, 2026

(54) CONTINUOUS PROCESS FOR THE PREPARATION OF EXO-TETRAHYDRODICYCLOPENTADIENE

(71) Applicants: CHINA PETROLEUM & CHEMICAL CORPORATION, Beijing (CN); SINOPEC RESEARCH INSTITUTE OF PETROLEUM PROCESSING CO., LTD., Beijing (CN)

(72) Inventors: Zhaolin Fu, Beijing (CN); Zhiping Tao, Beijing (CN); Enhui Xing, Beijing (CN); Yibin Luo, Beijing (CN); Xingtian Shu, Beijing (CN); Jie Zhao, Beijing (CN); Rui Yan, Beijing (CN); Dandan Jia, Beijing (CN); Zhongpeng Zhu, Beijing (CN); Weiping Zheng, Beijing (CN)

(73) Assignees: CHINA PETROLEUM & CHEMICAL CORPORATION, Beijing (CN); SINOPEC RESEARCH INSTITUTE OF PETROLEUM PROCESSING CO., LTD., Beijing (CN)

( * ) Notice: Subject to any disclaimer, the term of this patent is extended or adjusted under 35 U.S.C. 154(b) by 119 days.

(21) Appl. No.: 18/694,229

(22) PCT Filed: Sep. 23, 2022

(86) PCT No.: PCT/CN2022/120768
§ 371 (c)(1),
(2) Date: Mar. 21, 2024

(87) PCT Pub. No.: WO2023/046050
PCT Pub. Date: Mar. 30, 2023

(65) Prior Publication Data

US 2024/0294445 A1 Sep. 5, 2024

(30) Foreign Application Priority Data

Sep. 24, 2021 (CN) .......................... 202111120485.4

(51) Int. Cl.

| | |
|---|---|
| ***C07C 5/22*** | (2006.01) |
| ***B01J 21/08*** | (2006.01) |
| ***B01J 23/755*** | (2006.01) |
| ***B01J 29/12*** | (2006.01) |
| ***B01J 35/63*** | (2024.01) |
| ***B01J 37/10*** | (2006.01) |

(52) U.S. Cl.
CPC ............... *C07C 5/222* (2013.01); *B01J 21/08* (2013.01); *B01J 23/755* (2013.01); *B01J 29/126* (2013.01); *B01J 35/633* (2024.01); *B01J 37/10* (2013.01); *B01J 2229/186* (2013.01); *C07C 2529/08* (2013.01); *C07C 2529/12* (2013.01); *C07C 2529/14* (2013.01); *C07C 2529/16* (2013.01)

(58) Field of Classification Search
CPC . C07C 5/222; C07C 2529/08; C07C 2529/12; C07C 2529/14; C07C 2529/16; C07C 2521/08; C07C 2523/755; C07C 2603/68; C07C 5/03; C07C 5/13; C07C 7/12; C07C 7/163; C07C 13/61; C07C 2523/89; B01J 21/08; B01J 23/755; B01J 29/126; B01J 35/633; B01J 37/10; B01J 2229/186; B01J 23/42; B01J 23/89
See application file for complete search history.

(56) References Cited

U.S. PATENT DOCUMENTS

| | | | | |
|---|---|---|---|---|
| 4,086,284 A * | 4/1978 | Schneider | C07C 5/2253 585/905 |
| 4,270,014 A * | 5/1981 | Norton | C07C 5/2253 585/360 |
| 8,017,821 B2 | 9/2011 | Huang et al. | |
| 9,567,270 B1 * | 2/2017 | Mathur | C07C 5/2253 |
| 11,078,139 B1 * | 8/2021 | Harvey | C07C 1/24 |

(Continued)

FOREIGN PATENT DOCUMENTS

| | | |
|---|---|---|
| CN | 101244978 A | 8/2008 |
| CN | 101786936 B | 11/2012 |

(Continued)

OTHER PUBLICATIONS

Wang, Wenke et al., "Highly Efficient Hydroisomerization of Endo-Tetrahydrodicyclopentadiene to Exo-Tetrahydrodicyclopentadiene over Pt/HY", ACS Omega, vol. 6, No. 27, Jun. 30, 2021, pp. 17173-17182.

(Continued)

*Primary Examiner* — Ellen M McAvoy
(74) *Attorney, Agent, or Firm* — NKL Law; Allen Xue

(57) ABSTRACT

A continuous process for preparing exo-THDCPD by isomerization of endo-THDCPD includes the step of passing endo-THDCPD and hydrogen gas successively through a first reaction zone filled with a hydrogenation protectant and a second reaction zone filled with an isomerization catalyst to perform a hydroisomerization reaction so as to obtain exo-THDCPD, wherein the hydrogenation protectant is a supported metal hydrogenation catalyst, and the isomerization catalyst is a metal-modified molecular sieve catalyst. The process converts endo-THDCPD to exo-THDCPD, with a conversion of greater than 86% and a target product selectivity of greater than 94%.

16 Claims, No Drawings

(56) References Cited

U.S. PATENT DOCUMENTS

| | | | | |
|---|---|---|---|---|
| 2008/0064909 | A1* | 3/2008 | Huang | C07C 5/2266 585/377 |
| 2010/0249475 | A1* | 9/2010 | Huang | B01J 31/26 585/360 |
| 2011/0112346 | A1* | 5/2011 | Kawai | C07C 5/29 585/317 |

FOREIGN PATENT DOCUMENTS

| | | | |
|---|---|---|---|
| CN | 102924216 | A | 2/2013 |
| CN | 106669777 | A | 5/2017 |
| CN | 111939967 | A | 11/2020 |
| CN | 111943803 | A | 11/2020 |
| RU | 2191172 | C2 | 10/2002 |

OTHER PUBLICATIONS

Wang, Wei et al., “One-Step, Continuous-Flow, Highly Catalytic Hydrogenation—Isomerization of Dicyclopentadiene to exo-Tetrahydrodicyclopentadiene over Ni-Supported Catalysts for the Production of High-Energy-Density Fuel”, Energy & Fuels, vol. 27, No. 11, Aug. 13, 2013, pp. 6339-6347.

Xing, Enhui et al., “Endo- to exo-isomerization of tetrahydrodicyclopentadiene catalyzed by commercially available zeolites”, Journal of Molecular Catalysis A: Chemical, vol. 231, No. 1-2, Apr. 20, 2005, pp. 161-167.

* cited by examiner

CONTINUOUS PROCESS FOR THE PREPARATION OF EXO-TETRAHYDRODICYCLOPENTADIENE

TECHNICAL FIELD

This application relates to the technical field of isomerization of hydrocarbon compounds, specifically to a continuous process for preparing exo-tetrahydrodicyclopentadiene by isomerization of endo-tetrahydrodicyclopentadiene.

BACKGROUND OF ART

Dicyclopentadiene (DCPD) is mainly derived from the $C_5$ fraction that is a by-product of the petroleum cracking to ethylene process and the light benzene fraction that is a by-product of coal coking. It is a dimer of cyclopentadiene and is an important chemical intermediate that is widely used in the synthesis of unsaturated polyester polymers, preparation of high-density aviation fuel, preparation of medical materials, etc. Its fully hydrogenated product endo-tetrahydrodicyclopentadiene (endo-THDCPD) is a solid high-density fuel with excellent performance, but it cannot be used as a liquid fuel. Its isomerization product exo-tetrahydrodicyclopentadiene (exo-THDCPD) has merits such as relatively large density (0.94 $g/cm^{-3}$), low freezing point (<−79° C.), high volume calorific value (39.4 MJ/L) and low toxicity. It can be used alone or in combination. It is a liquid fuel with excellent comprehensive properties and has been widely researched and applied in the field of aviation fuel. The common preparation process of exo-THDCPD is a two-step conversion process in which DCPD is first hydrogenated to prepare endo-THDCPD and then endo-THDCPD is isomerized to exo-THDCPD.

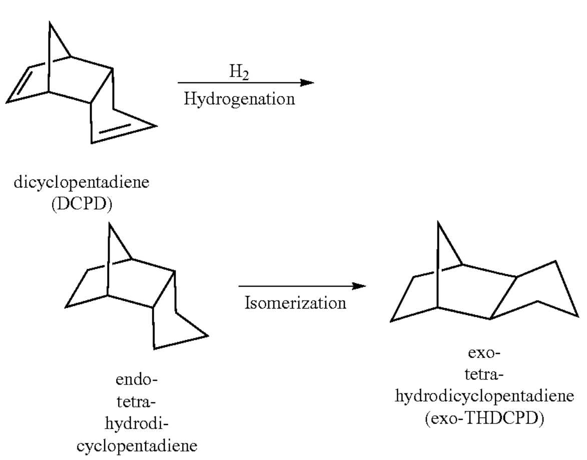

The hydrogenation process is relatively mature and can be completed through conventional supported hydrogenation catalysts or Raney nickel catalysts. However, the industrial isomerization process still needs to be carried out intermittently using highly toxic and highly polluting $AlCl_3$ as a catalyst. Continuous industry production has not been achieved up to now. As described in U.S. Pat. No. 9,567,270B1, the isomerization process still requires aluminum halide such as $AlCl_3$ as a catalyst, resulting in a low output of exo-THDCPD, serious pollution in the production process, and complex post-processing, limiting its large-scale application. There are also related studies using acidic ionic liquids as catalysts to catalyze endo-THDCPD isomerization as described in U.S. Pat. No. 8,017,821 B2. However, the ionic liquid itself suffers from complex preparation process, high cost, and poor industrial application capabilities.

In addition, although some studies use molecular sieves as isomerization catalysts, such as patent CN 101786936B, which uses Y, Beta, mordenite, Al-MCM-41, Al-MCM-48, Al-SBA-15, etc. as isomerization catalysts, however only the conversion rate of raw materials and the product yield are investigated without involving the issue of the catalyst life and the possibility of the continuous production, therefore the practical application capabilities have not been proved yet.

SUMMARY OF THE INVENTION

This application aims at the problem that existing industries cannot continuously and stably produce exo-THDCPD and provides a process for continuous long-cycle production of exo-THDCPD in a fixed-bed reactor.

To achieve the above object, this application provides a continuous process for preparing exo-THDCPD by isomerization of endo-THDCPD, which comprises passing endo-THDCPD and hydrogen gas successively through a first reaction zone filled with a hydrogenation protectant and a second reaction zone filled with an isomerization catalyst to perform a hydroisomerization reaction so as to obtain exo-THDCPD, wherein the hydrogenation protectant is a supported metal hydrogenation catalyst, and the isomerization catalyst is a metal-modified molecular sieve catalyst.

The process of this application performs the hydroisomerization reaction of endo-THDCPD by passing the liquid reaction raw materials successively through two reaction zones filled with the hydrogenation protectant and the isomerization catalyst respectively, so that the service life and process stability of the used isomerization catalyst have been improved greatly, and a green, continuous and stable preparation of exo-THDCPD has been achieved. The conversion rate is greater than 86%, the selectivity of the target product is greater than 94%, and a continuous operation of more than 2000 hours can be achieved. It has an industrial application prospect.

Other features and advantages of the present application will be described in detail in the subsequent detailed description.

DETAILED DESCRIPTION

The specific implementation manners of this application are described in detail below. It should be understood that the specific implementation manners described herein are only used to illustrate and explain this application, and are not used to limit this application.

Any specific numerical value disclosed herein (including the endpoints of a numerical range) is not limited to the precise value of the numerical value but is to be understood to further cover values close to the precise value, e.g. all possible values within ±5% of the precise value. Moreover, for the disclosed numerical ranges, one or more new numerical ranges can be obtained by any combination between the endpoint values of the ranges, between one endpoint value of the ranges and one specific point value within the ranges, and between any two specific point values of the ranges. These new numerical ranges shall also be deemed to be specifically disclosed herein.

Unless otherwise stated, the terms used herein have the same meanings as commonly understood by those skilled in the art. If a term is defined herein and its definition is different from the common understanding in the art, the definition herein shall prevail.

In this application, unless expressly stated, any issues or matters not mentioned shall directly apply to those known in the art without any change. Moreover, any embodiment described herein can be freely combined with one or more other embodiments described herein, and the technical solutions or technical ideas thus formed shall be regarded as part of the original disclosure or original content of this application and shall not be considered to be a new matter that has not been disclosed or expected herein unless those skilled in the art believe that the combination is obviously unreasonable.

In this application, unless otherwise stated, the given pressure values are gauge pressures.

In this application, unless otherwise stated, the given metal contents of the hydrogenation protectant and the isomerization catalyst are based on metal elements.

In this application, the term "hydrogen/liquid volume ratio" refers to the volume ratio of hydrogen gas to liquid material in the reaction system, in unit of $Nm^3/m^3$.

All patents and non-patent literature including but not limited to textbooks and journal articles mentioned herein are incorporated by reference in their entirety.

As stated above, this application provides a continuous process for preparing exo-THDCPD by isomerization of endo-THDCPD, which comprises passing endo-THDCPD and hydrogen gas successively through a first reaction zone filled with a hydrogenation protectant and a second reaction zone filled with an isomerization catalyst to perform a hydroisomerization reaction so as to obtain exo-THDCPD, wherein the hydrogenation protectant is a supported metal hydrogenation catalyst, and the isomerization catalyst is a metal-modified molecular sieve catalyst.

In the method of this application, the function of the hydrogenation protectant filled in the first reaction zone is to remove trace impurities such as olefins in the raw material endo-THDCPD by hydrogenation and activate the hydrogen gas, thereby protecting the isomerization catalyst, inhibiting its coking, and prolonging its period of service.

According to this application, the hydrogenation protectant can be a conventional supported metal hydrogenation catalyst, and this application does not have strict limitations thereon. In a preferable embodiment, based on the total mass of the hydrogenation protectant, the hydrogenation protectant contains 0.1-30 wt % of an active metal selected from Pd, Pt, Ru, Rh, Ni, Cu or combinations thereof, and 70-99.9 wt % of a non-acidic support selected from $Al_2O_3$, $SiO_2$, $ZrO_2$, $TiO_2$, $CeO_2$, activated carbon or combinations thereof. Further preferably, based on the total mass of the hydrogenation protectant, the total content of Ni and Cu is 5-20 wt %, and the total content of Pd, Pt, Ru, and Rh is 0.3-3 wt %.

In the process of this application, the isomerization reaction in the second reaction zone is performed in the presence of a metal-modified molecular sieve catalyst, which has the dual functions of isomerization and coking inhibition. By loading the modifying metal on the molecular sieve, the molecular sieve exhibits a stable isomerization activity, while the modifying metal does not participate in the isomerization reaction, but inhibits the generation of coking precursors (olefin intermediates) during the reaction, thereby increasing the catalyst lifetime. According to this disclosure, the isomerization catalyst is a metal-modified molecular sieve catalyst. Preferably, based on the total mass of the isomerization catalyst, the isomerization catalyst contains 0.05-20 wt %, preferably 0.1-15 wt %, more preferably 0.2-10 wt % of a modifying metal selected from Pd, Pt, Ru, Rh, Ni or combination thereof, and 80-99.95 wt %, preferably 85-99.9 wt %, more preferably 90-99.8 wt % of a Y-type molecular sieve. Further preferably, based on the total mass of the isomerization catalyst, the content of Ni is 1-20 wt %, preferably 3-15 wt %, more preferably 5-10 wt %; the total content of Pd, Pt, Ru, and Rh is 0.05-3 wt %, preferably 0.1-1.0 wt %, more preferably 0.2-0.5 wt %.

In a further preferable embodiment, based on the total mass of the isomerization catalyst, the catalyst has a sodium content (as sodium oxide) of 0-1.0 wt %, preferably 0-0.5 wt %, more preferably 0-0.2 wt %, e.g., 0-0.1 wt %.

In a particularly preferable embodiment, the modifying metal is selected from Pt, Pd and combinations thereof; the Y-type molecular sieve is selected from HY, USY, REHY or combinations thereof.

In a further preferable embodiment, the Y-type molecular sieve used in the isomerization catalyst is subjected to a pressurized hydrothermal calcining treatment in a water vapour atmosphere, wherein the treatment temperature is 450-650° C., preferably 500-600° C., the treatment pressure is 0-0.5 MPa, preferably 0.1-0.3 MPa, and the treatment time is 1-6 h, preferably 2-4 h, to achieve the pore expansion of the molecular sieve, increase the mesopore volume, and enhance the effect of the material diffusion. In a further preferable embodiment, the Y-type molecular sieve is further subjected to an ammonium exchange after the hydrothermal calcining treatment, so that its sodium content (as sodium oxide) is reduced to 1.0 wt % or less, preferably 0.5 wt % or less, more preferably 0.2 wt % or less, e.g., 0.05 wt %, 0.1 wt %, 0.15 wt %, etc.

According to this application, the metal-modified molecular sieve catalyst can be prepared according to conventional methods, such as the isometric impregnation method, the excess volume impregnation method, etc. In some specific embodiments, the metal-modified molecular sieve catalyst can be prepared as follows: preparing a certain amount of a metal precursor solution according to the metal loading amount, then impregnating the molecular sieve in the metal precursor solution and letting the solution stand at normal temperature for more than 6 hours with intermittently stirring during the impregnation; then drying at 80° C. for more than 10 hours, and then calcining at 450-550° C. for 2-5 hours in an air atmosphere; reducing the calcined catalyst in a reducing atmosphere such as hydrogen gas at 400-550° C. for 2-5 hours to produce an activated catalyst. This application does not have strict limitations on the metal precursor used, which can be selected from soluble salts of the corresponding metals, including but not limited to nitrates, sulfates, chlorides, and the like.

In a preferable embodiment, as determined by the BET method, the isomerization catalyst has a total pore volume of 0.15-0.80 $cm^3/g$, preferably 0.25-0.50 $cm^3/g$, and a mesopore volume of 0.015-0.15 $cm^3/g$, preferably 0.02-0.05 $cm^3/g$.

In a preferable embodiment, the reaction temperature in the first reaction zone is 100-200° C., preferably 130-170° C.; the reaction temperature in the second reaction zone is 100-180° C., preferably 130-170° C.

In a preferable embodiment, in the first and second reaction zones, the reaction pressure is 0.1-3.0 MPa, preferably 0.5-1.0 MPa; the WHSV (weight hourly space velocity) is 0.2-5 $h^{-1}$, preferably 0.5-2 $h^{-1}$; the hydrogen/liquid volume ratio is 100-3200 $Nm^3/m^3$, preferably 600-1200 $Nm^3/m^3$. Further preferably, the reaction in the first and second reaction zones is carried out in a hydrogen gas atmosphere, and the reaction pressure in this case is the hydrogen gas pressure.

According to this application, the endo-THDCPD used as a raw material for the isomerization reaction can be purchased commercially or can be prepared according to various methods disclosed in the prior art.

In a preferable embodiment, the endo-THDCPD is mixed with a solvent before the reaction to obtain a mixed material with a mass concentration of endo-THDCPD of 10-80 wt %, preferably 30-60 wt %, and then the reaction is carried out. Further preferably, the solvent is a hydrocarbon or halogenated hydrocarbon solvent with a boiling point of 40-300° C., e.g., cyclohexane, methylcyclohexane, dichloromethane, and the like, preferably $C_6$-$C_{10}$ hydrocarbons, more preferably selected from cyclohexane, methylcyclohexane, exo-THDCPD or combinations thereof.

In a preferable embodiment, the endo-THDCPD or the mixed material is pretreated with an adsorbent before the reaction. Preferably, the adsorbent may be materials that can adsorb polar compounds, such as activated clay, NaY molecular sieve, HY molecular sieve, and activated carbon, more preferably activated clay and NaY molecular sieve.

In a further preferable embodiment, the pretreatment conditions include temperature: from normal temperature to 60° C., pressure: 0-0.5 MPa, and WHSV: 0.1-5.0 $h^{-1}$.

In a preferable embodiment, the process of this application is carried out using a fixed-bed reactor, and the first reaction zone is arranged above the second reaction zone, preferably, the first reaction zone and the second reaction zone are separated by an inert material.

In some preferable embodiments, the process of this application includes passing endo-THDCPD and a reaction solvent into a pretreatment reactor provided with an adsorbent for pretreatment, and the effluent entering into a fixed-bed reactor to perform a hydroisomerization reaction to produce exo-THDCPD, wherein in the fixed-bed reactor, the upper section is provided with a hydrogenation protectant and the lower section is provided with an isomerization catalyst.

In this embodiment, endo-THDCPD and the reaction solvent are uniformly premixed in a raw material tank, and then flow from an upper end of a pretreatment reactor provided with an adsorbent into the pretreatment reactor at normal temperature and normal pressure; the resulting impurity-removed material flows out from a lower end of the pretreatment reactor and is then pumped to an upper end of the fixed-bed reactor and passed together with hydrogen gas through a reaction bed of the hydrogenation protectant and a reaction bed of the isomerization catalyst successively; and the resulting reaction products flow out from a lower end of the fixed bed.

In this embodiment, the function of the pretreatment reactor is to fully contact the solid material with the liquid, and the pretreatment reactor can be selected from fixed-bed reactors or quartz glass tubes, etc.

In a particularly preferable embodiment, the process of this application includes: endo-THDCPD and a reaction solvent are firstly mixed uniformly; the resulting mixture is passed into a pretreatment reactor, where impurities are removed by adsorption with an adsorbent such as activated clay and NaY; then the resulting impurity-removed material flows in from an upper end of a fixed-bed reactor and flows out from its lower end, wherein in the fixed-bed reactor, the upper section is provided with a hydrogenation protectant and the lower section is provided with an isomerization catalyst; the hydrogenation reaction temperature in the upper section is 100-200° C., and the isomerization reaction temperature in the lower section is 100-180° C., the reaction pressure of the entire fixed-bed reactor is 0.1-3.0 MPa, the WHSV is 0.2-5 $h^{-1}$, and the hydrogen/liquid volume ratio is 100-3200 $Nm^3/m^3$.

EXAMPLES

This application will be further described below in conjunction with the examples, but they do not constitute any limitation to the present applications.

In the following example, endo-THDCPD was purchased from Beijing Innochem Science and Technology Co. Ltd. and had a purity of >99%, an olefin content of <1%, a total sulfur content of <100 ppm, and a total nitrogen content of <100 ppm.

In the following Examples and Comparative Examples, if not otherwise indicated, the hydroisomerization reaction of endo-THDCPD was carried out in a fixed-bed reactor under a hydrogen gas atmosphere, in which the hydrogen gas and liquid material were passed through the fixed-bed reactor from top to bottom, and the upper section of the reactor (also called as the hydrogenation section herein) was filled with a hydrogenation protectant, the lower section of the reactor (also called as the isomerization section herein) was filled with an isomerization catalyst and quartz sand was filled as an inert material between the hydrogenation section and the isomerization section. In addition, an effluent of the fixed-bed reactor was sampled and analyzed by gas chromatography, and the reactant conversion rate and product selectivity were calculated based on the area normalization method. The fixed-bed reactor was a tubular reactor with a length of 1 m and an inner diameter of 9 mm. The catalyst was loaded in the middle of the fixed-bed reactor.

In the following Examples and Comparative Examples, the used HY molecular sieve, REHY molecular sieve, USY molecular sieve, HZSM-5 molecular sieve and Hβ molecular sieve were purchased from a branch of Sinopec Catalyst Co., Ltd.

Unless otherwise indicated, various reagents used in the following Examples and Comparative Examples were commercially available products with purity of analytical grade.

Example 1

A solution containing 50 wt % endo-THDCPD in methylcyclohexane without pretreatment as a raw material was pumped directly into the fixed-bed reactor. The hydrogenation protectant was 20 wt % $Ni/SiO_2$, and the reaction temperature of the hydrogenation section was 150° C. The isomerization catalyst was 0.3 wt % Pt/HY (having a $Na_2O$ content of 0.156%), and the reaction temperature of the isomerization section was 150° C. The reaction pressure of the entire fixed bed was 0.5 MPa, the WHSV was 2 $h^{-1}$, and the hydrogen/liquid volume ratio was 1000 $Nm^3/m^3$. After a 200 h reaction, a sample was taken for analysis. The results were shown in Table 1.

Comparative Example 1

Comparative Example 1 was conducted with reference to Example 1 except that no hydrogenation section was provided in the fixed-bed reactor. After a 200 h reaction, a sample was taken for analysis. The results were shown in Table 1.

TABLE 1

Reaction Results of Example 1 and Comparative Example 1

| Example No. | Endo-THDCPD conversion (%) | Exo-THDCPD selectivity (%) | Adamantane selectivity (%) | Ring-opening by-product selectivity (%) |
|---|---|---|---|---|
| Example 1 | 71 | 96.1 | 0.5 | 3.4 |
| Comparative Example 1 | 48 | 98.4 | 0.2 | 1.4 |

Examples 2-4

In the pretreatment reactor, a solution containing 50 wt % endo-THDCPD in methylcyclohexane was used as a raw material and flowed through the pretreatment reactor provided with different adsorbents at normal temperature and normal pressure with the WHSV of 0.5 $h^{-1}$. After the pretreatment, the resulting material was pumped into the fixed-bed reactor. In the fixed-bed reactor, the solution containing 50 wt % endo-THDCPD in methylcyclohexane treated with different pretreatment manners was used as a raw material. The hydrogenation protectant was 20 wt % $Ni/SiO_2$, and the reaction temperature of the hydrogenation section was 150° C. The isomerization catalyst was 0.3 wt % Pt/HY (having a $Na_2O$ content of 0.156%), and the reaction temperature of the isomerization section was 150° C. The reaction pressure of the entire fixed bed was 0.5 MPa, the WHSV was 2 $h^{-1}$, and the hydrogen/liquid volume ratio was 1000 $Nm^3/m^3$. After a 200 h reaction, a sample was taken for analysis. The effect of the pretreatment manner on the reaction results was examined. The results were shown in Table 2.

TABLE 2

Reaction Results of Examples 2-4

| Example No. | Pretreatment manner | Endo-THDCPD conversion (%) | Exo-THDCPD selectivity (%) | Adamantane selectivity (%) | Ring-opening by-product selectivity (%) |
|---|---|---|---|---|---|
| 2 | Pretreated with NaY | 91 | 93.2 | 0.6 | 6.2 |
| 3 | Pretreated with activated clay | 90 | 93.3 | 0.7 | 6.0 |
| 4 | Pretreated with HY | 76 | 95.8 | 0.4 | 3.8 |

Examples 5-7

In the pretreatment reactor, a solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the isomerization catalyst was 0.3 wt % Pt/HY (having a $Na_2O$ content of 0.156%), and the reaction temperature of the isomerization section was 150° C. The composition of the hydrogenation protectant and the temperature of the hydrogenation section were shown in Table 3. The reaction pressure was 0.5 MPa, the WHSV was 2 $h^{-1}$, and the hydrogen/liquid volume ratio was 1000 $Nm^3/m^3$. After a 300 h reaction, a sample was taken for analysis. The effect of the hydrogenation protectant on the reaction results was examined. The results were shown in Table 3.

Comparative Example 2

Comparative Example 2 was conducted with reference to Example 5 except that no hydrogenation section was provided in the fixed-bed reactor. After a 200 h reaction, a sample was taken for analysis. The results were shown in Table 3.

TABLE 3

Reaction Results of Examples 5-7 and Comparative Example 2

| Example No. | Hydrogenation protectant | Hydrogenation section temperature (° C.) | Endo-THDCPD conversion (%) | Exo-THDCPD selectivity (%) | Adamantane selectivity (%) | Ring-opening by-product selectivity (%) |
|---|---|---|---|---|---|---|
| Example 5 | 20 wt % $Ni/SiO_2$ | 150 | 91 | 93.4 | 0.5 | 6.1 |
| Example 6 | 20 wt % $Ni/SiO_2$ | 100 | 84 | 95.3 | 0.5 | 4.2 |
| Example 7 | 20 wt % $Ni/SiO_2$ | 200 | 93 | 83.6 | 1.5 | 14.9 |
| Comparative Example 2 | No | No | 60 | 97.3 | 0.3 | 2.4 |

Examples 8-10

A solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. Different molecular sieves loaded with 0.3% Pt were used as the isomerization catalysts, and the reaction temperature of the isomerization section was 150° C. The reaction pressure of the entire fixed bed was 0.5 MPa, the WHSV was 2 $h^{-1}$, and the hydrogen/liquid volume ratio was 1000 $Nm^3/m^3$. After a 200 h reaction, a sample was taken for analysis. The endo-THDCPD isomerization activity and the stability of isomerization catalysts based on different molecular sieves were examined. The results were shown in Table 4.

Comparative Examples 3-4

Comparative Examples 3-4 were conducted with reference to Example 8 except that isomerization catalysts different from that of Example 8 were used. After a 200 h reaction, a sample was taken for analysis. The results were shown in Table 4.

TABLE 4

Reaction Results of Examples 8-10 and Comparative Examples 3-4

| Example No. | Isomerization molecular sieve | Endo-THDCPD conversion (%) | Exo-THDCPD selectivity (%) | Adamantane selectivity (%) | Ring-opening by-product selectivity (%) |
|---|---|---|---|---|---|
| Example 8 | HY | 91 | 93.2 | 0.6 | 6.2 |
| Example 9 | REHY | 88 | 95.8 | 0.3 | 3.9 |
| Example 10 | USY | 90 | 93.9 | 0.4 | 5.7 |
| Comparative Example 3 | HZSM-5 | 32 | 98.3 | 0.2 | 1.5 |
| Comparative Example 4 | Hβ | 48 | 98.6 | 0.2 | 1.2 |

Examples 11-19

A REHY molecular sieve was subjected to the hydrothermal calcining treatment under different conditions, followed by an ammonium exchange, and then loaded with 0.3% Pt to prepare different isomerization catalysts, requiring $Na_2O$ %<0.2%. The obtained catalysts were subjected to a BET analysis to examine the change in their pore structure, and then subjected to the examination of the catalyst performance according to the conditions in Example 2 except that the reaction temperature of the isomerization section was adjusted to 170° C. to increase the severity of the reaction. After a 200 h reaction, a sample was taken for analysis. The effect of different hydrothermal calcining treatment conditions on the activity of the isomerization catalyst was examined. The results were shown in Table 5.

TABLE 5

Reaction Results of Examples 11-19

| Example No. | Hydrothermal calcining temperature (° C.) | Hydrothermal calcining pressure (MPa) | Hydrothermal calcining time (h) | Total pore volume ($cm^3/g$) | Mesopore volume ($cm^3/g$) | Endo-THDCPD conversion (%) | Exo-THDCPD selectivity (%) | Adamantane selectivity (%) | Ring-opening by-product selectivity (%) |
|---|---|---|---|---|---|---|---|---|---|
| Example 11 | 450 | 0.3 | 2 | 0.352 | 0.030 | 82 | 88.8 | 3.7 | 7.5 |
| Example 12 | 500 | 0.3 | 2 | 0.346 | 0.032 | 94 | 87.9 | 4.2 | 7.9 |
| Example 13 | 550 | 0.3 | 2 | 0.338 | 0.037 | 95 | 87.6 | 4.5 | 7.9 |
| Example 14 | 600 | 0.3 | 2 | 0.308 | 0.035 | 89 | 88.7 | 4.1 | 7.2 |
| Example 15 | 550 | 0.0 | 2 | 0.332 | 0.030 | 80 | 89.2 | 3.4 | 7.4 |
| Example 16 | 550 | 0.5 | 2 | 0.301 | 0.029 | 76 | 90.6 | 3.1 | 6.3 |
| Example 17 | 550 | 0.3 | 1 | 0.346 | 0.034 | 81 | 89.5 | 3.7 | 6.8 |
| Example 18 | 550 | 0.3 | 4 | 0.329 | 0.035 | 88 | 89.0 | 4.1 | 6.9 |
| Example 19 | 550 | 0 | 0 | 0.295 | 0.027 | 70 | 91.5 | 2.8 | 5.7 |

Examples 20-23

The REHY molecular sieves obtained after the hydrothermal calcining treatment under the conditions of 550° C., 0.3 MPa, and 2 hours in Example 13 was subjected to an ammonium exchange, but the $Na_2O$ content was controlled to prepare the REHY molecular sieves with different $Na_2O$ contents, and then the corresponding isomerization catalysts were prepared according to the process described in Example 13. The catalyst performance was evaluated according to the method in Example 9. After a 200 h reaction, a sample was taken for analysis. The effect of different $Na_2O$ contents on the activity of the isomerization catalysts was examined. The results were shown in Table 6.

TABLE 6

Reaction Results of Examples 20-22

| Example No. | $Na_2O$ content (%) | Endo-THDCPD conversion (%) | Exo-THDCPD selectivity (%) | Adamantane selectivity (%) | Ring-opening by-product selectivity (%) |
|---|---|---|---|---|---|
| Example 20 | 0.096 | 95 | 94.4 | 0.6 | 5.0 |
| Example 21 | 0.182 | 88 | 95.8 | 0.3 | 3.9 |

TABLE 6-continued

Reaction Results of Examples 20-22

| Example No. | $Na_2O$ content (%) | Endo-THDCPD conversion (%) | Exo-THDCPD selectivity (%) | Adamantane selectivity (%) | Ring-opening by-product selectivity (%) |
|---|---|---|---|---|---|
| Example 22 | 0.360 | 81 | 97.3 | 0.2 | 2.5 |
| Example 23 | 0.621 | 68 | 98.1 | 0.2 | 1.7 |

Examples 24-28

The REHY molecular sieve with a $Na_2O$ % content of 0.182% obtained after the hydrothermal calcining treatment and the ammonium exchange in Example 21 was loaded with different metals to obtain isomerization catalysts. The catalyst performance was then evaluated according to the method in Example 9. After a 200 h reaction, a sample was taken for analysis. The effect of different modifying metals and content thereof on the activity of the isomerization catalysts was examined. The results were shown in Table 7.

TABLE 7

Reaction Results of Examples 24-28

| Example No. | Metal type and loading amount | Endo-THDCPD conversion (%) | Exo-THDCPD selectivity (%) | Adamantane selectivity (%) | Ring-opening by-product selectivity (%) |
|---|---|---|---|---|---|
| Example 24 | 0.1% Pt | 73 | 97.8 | 0.2 | 2.0 |
| Example 25 | 0.3% Pt | 88 | 95.8 | 0.3 | 3.9 |
| Example 26 | 0.5% Pt | 88 | 96.0 | 0.2 | 3.8 |
| Example 27 | 5.0% Ni | 85 | 96.2 | 0.2 | 3.6 |
| Example 28 | 10.0% Ni | 86 | 96.1 | 0.2 | 3.7 |

Examples 29-32

A solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. The isomerization catalyst was 0.3 wt % Pt/HY (having a $Na_2O$ content of 0.156%). The reaction pressure of the entire fixed bed was 0.5 MPa, the WHSV was 1 $h^{-1}$, and the hydrogen/liquid volume ratio was 1000 $Nm^3/m^3$. After a 20 h reaction, a sample was taken for analysis. The obtained analysis results could be regarded as the initial conversion rate and selectivity. The effect of the isomerization reaction temperature on the reaction results was examined. The results were shown in Table 8.

TABLE 8

Reaction Results of Examples 29-32

| Example No. | Isomerization section reaction temperature (° C.) | Endo-THDCPD conversion (%) | Exo-THDCPD selectivity (%) | Adamantane selectivity (%) | Ring-opening by-product selectivity (%) |
|---|---|---|---|---|---|
| Example 29 | 100 | 67 | 97.7 | 0.2 | 2.1 |
| Example 30 | 120 | 82 | 96.8 | 0.4 | 2.8 |
| Example 31 | 150 | 93 | 92.2 | 0.7 | 7.1 |
| Example 32 | 180 | 95 | 74.7 | 6.3 | 19.0 |

Examples 33-36

A solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. The isomerization catalyst was 0.3 wt % Pt/HY. The reaction temperature of the isomerization section was 150° C., the WHSV was 1 $h^{-1}$, and the hydrogen/liquid volume ratio was 1000 $Nm^3/m^3$. After a 20 h reaction, a sample was taken for analysis. The obtained analysis results could be regarded as the initial conversion rate and selectivity. The effect of the system reaction pressure on the reaction results was examined. The results were shown in Table 9.

TABLE 9

| Reaction Results of Examples 33-36 | | | | | |
|---|---|---|---|---|---|
| Example No. | Reaction pressure (MPa) | Endo-THDCPD conversion (%) | Exo-THDCPD selectivity (%) | Adamantane selectivity (%) | Ring-opening by-product selectivity (%) |
| Example 33 | 0.2 | 85 | 95.2 | 0.3 | 4.5 |
| Example 34 | 0.5 | 93 | 92.2 | 0.7 | 7.1 |
| Example 35 | 1.0 | 95 | 83.9 | 0.7 | 15.4 |
| Example 36 | 2.0 | 95 | 72.0 | 0.9 | 27.1 |

Examples 37-40

A solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. The isomerization catalyst was 0.3 wt % Pt/HY, and the reaction temperature of the isomerization section was 150° C. The reaction pressure of the entire fixed bed was 0.5 MPa, and the hydrogen/liquid volume ratio was 1000 $Nm^3/m^3$. After a 20 h reaction, a sample was taken for analysis. The obtained analysis results could be regarded as the initial conversion rate and selectivity. The effect of the WHSV on the reaction results was examined. The results were shown in Table 10.

TABLE 10

| Reaction Results of Examples 37-40 | | | | | |
|---|---|---|---|---|---|
| Example | WHSV ($h^{-1}$) | Endo-THDCPD conversion (%) | Exo-THDCPD selectivity (%) | Adamantane selectivity (%) | Ring-opening by-product selectivity (%) |
| Example 37 | 0.5 | 95 | 90.1 | 0.9 | 9.0 |
| Example 38 | 1.0 | 93 | 92.2 | 0.7 | 7.1 |
| Example 39 | 2.0 | 91 | 92.9 | 0.6 | 6.5 |
| Example 40 | 3.0 | 85 | 94.7 | 0.5 | 4.8 |

Examples 41-43

A solution containing 50 wt % endo-THDCPD in methylcyclohexane was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. The isomerization catalyst was 0.3 wt % Pt/HY, and the reaction temperature of the isomerization section was 150° C. The reaction pressure of the entire fixed bed was 0.5 MPa, and the WHSV was 1 $h^{-1}$. After a 20 h reaction, a sample was taken for analysis. The obtained analysis results could be regarded as the initial conversion rate and selectivity. The effect of the hydrogen/liquid volume ratio on the reaction results was examined. The results were shown in Table 11.

TABLE 11

| Reaction Results of Examples 41-43 | | | | | |
|---|---|---|---|---|---|
| Example No. | Hydrogen/liquid volume ratio, $Nm^3/m^3$ | Endo-THDCPD conversion (%) | Exo-THDCPD selectivity (%) | Adamantane selectivity (%) | Ring-opening by-product selectivity (%) |
| Example 41 | 500 | 93 | 91.2 | 0.8 | 8.0 |
| Example 42 | 1000 | 93 | 92.2 | 0.7 | 7.1 |
| Example 43 | 1500 | 93 | 92.7 | 0.7 | 6.6 |

Examples 44-47

A solution containing endo-THDCPD with different mass concentrations was used as a raw material. After pre-mixing uniformly and pretreating with NaY to remove impurities, the resulting impurity-removed material was pumped into the fixed-bed reactor. In the fixed-bed reactor, the hydrogenation protectant was 20 wt % $Ni/SiO_2$, and the temperature of the hydrogenation section was 150° C. The isomerization catalyst was 0.3 wt % Pt/HY, and the reaction temperature of the isomerization section was 150° C. The reaction pressure of the entire fixed bed was 0.5 MPa, the WHSV was 1 $h^{-1}$, and the hydrogen/liquid volume ratio was 1000 $Nm^3/m^3$. After a 20 h reaction, a sample was taken for analysis. The obtained analysis results could be regarded as the initial conversion rate and selectivity. The effect of different reaction solvents and raw material mass concentrations on the reaction results was examined. The results were shown in Table 12.

TABLE 12

Reaction Results of Examples 44-47

| Example No. | Reaction solvent | Mass concentration (wt %) | Endo-THDCPD conversion (%) | Exo-THDCPD selectivity (%) | Adamantane selectivity (%) | Ring-opening by-product selectivity (%) |
|---|---|---|---|---|---|---|
| Example 44 | methylcyclohexane | 50 | 93 | 92.2 | 0.7 | 7.1 |
| Example 45 | dichloromethane | 50 | 95 | 91.0 | 1.0 | 8.0 |
| Example 46 | methylcyclohexane | 80 | 94 | 89.7 | 1.2 | 9.1 |
| Example 47 | methylcyclohexane | 10 | 93 | 94.3 | 0.6 | 5.1 |

Example 48

The operation cycle of Example 5 was further extended to 2000 h, and it was found that the endo-THDCPD conversion slowly dropped to 86%, the exo-THDCPD selectivity slowly increased to 94.5%, the adamantane selectivity slowly dropped to 0.3%, and the ring-opening by-product selectivity slowly dropped to 5.2%, indicating that the reaction system operating the process of this application had excellent stability.

The preferred embodiments of this application have been described in detail above. However, this application is not limited to the specific details in the above-mentioned embodiments. Within the scope of the technical concept of this application, a variety of simple modifications can be made to the technical solutions of this application. These simple modifications all fall within the protection scope of this application.

In addition, it should be noted that each of the specific technical features described in the above-mentioned specific embodiments can be combined in any suitable manner without conflict. To avoid unnecessary repetition, various possible combinations will not be further described in this application.

In addition, any combinations can be also made between various embodiments of this application, as long as they do not violate the idea of this application; and they should also be regarded as the invention contents of this application.

The invention claimed is:

1. A continuous process for preparing exo-tetrahydrodicyclopentadiene by isomerization of endo-tetrahydrodicyclopentadiene, comprising:

passing hydrogen and a feedstock comprising endo-tetrahydrodicyclopentadiene successively through a first reaction zone filled with a hydrogenation protectant and a second reaction zone filled with an isomerization catalyst to perform a hydroisomerization reaction to obtain exo-tetrahydrodicyclopentadiene, wherein the hydrogenation protectant is a supported metal hydrogenation catalyst, and the isomerization catalyst is a metal-modified molecular sieve catalyst.

2. The process according to claim 1, wherein, based on the total mass of the hydrogenation protectant, the hydrogenation protectant contains 0.1-30 wt % of an active metal selected from Pd, Pt, Ru, Rh, Ni, Cu, and combinations thereof, and 70-99.9 wt % of a non-acidic support selected from $Al_2O_3$, $SiO_2$, $ZrO_2$, $TiO_2$, $CeO_2$, activated carbon, and combinations thereof.

3. The process according to claim 1, wherein, based on the total mass of the isomerization catalyst, the isomerization catalyst contains 0.05-20 wt % a modifying metal selected from Pd, Pt, Ru, Rh, Ni, and combination thereof, and 80-99.95 wt % of a Y-type molecular sieve, wherein the Y-type molecular sieve is selected from HY, USY, REHY, and combinations thereof.

4. The process according to claim 3, wherein, based on the total mass of the isomerization catalyst, the content of Ni is 1-20 wt %, and the total content of Pd, Pt, Ru, and Rh is 0.05-3 wt %.

5. The process according to claim 3, wherein, the Y-type molecular sieve used in the isomerization catalyst is subjected to a pressurized hydrothermal calcining treatment in a water vapour atmosphere, at 450-650° C. under a pressure of 0-0.5 MPa, for 1-6 h.

6. The process according to claim 1, wherein the feedstock further comprises a hydrocarbon or halogenated hydrocarbon solvent with a boiling point of 40-300° C., and a mass concentration of endo-tetrahydrodicyclopentadiene in the feedstock is 10-80 wt %.

7. The process according to claim 1, further comprising pretreating the feedstock with an adsorbent before the reaction.

8. The process according to claim 7, wherein the pretreatment is conducted under a temperature of from normal temperature to 60° C., a pressure of 0-0.5 MPa, and at a weight hourly space velocity of 0.1-5.0 $h^{-1}$.

9. The process according to claim 1, wherein the reaction temperature in the first reaction zone is 100-200° C., and the reaction temperature in the second reaction zone is 100-180° C.

10. The process according to claim 1, wherein in the first reaction zone or the second reaction zones, the reaction pressure is 0.1-3.0 MPa, the weight hourly space velocity is 0.2-5 $h^{-1}$, and the hydrogen/liquid volume ratio is 100-3200.

11. The process according to claim 1, wherein the process is carried out in a fixed-bed reactor comprising the first reaction zone disposed above the second reaction zone.

12. The process according to claim 2, wherein, based on the total mass of the hydrogenation protectant, the total content of Ni and Cu is 5-20 wt %, and the total content of Pd, Pt, Ru, and Rh is 0.3-3 wt %.

13. The process according to claim 1, wherein, based on the total mass of the isomerization catalyst, the catalyst has a sodium content as sodium oxide of 0-1.0 wt %.

14. The process according to claim 6, wherein the solvent is selected from C6-C10 hydrocarbons and mixtures thereof.

15. The process according to claim 7, wherein the adsorbent is selected from activated clay, NaY molecular sieve, HY molecular sieve, activated carbon, and combinations thereof.

16. The process according to claim 11, wherein the first reaction zone and the second reaction zone are separated by an inert material.

* * * * *